United States Patent
Yakimoski et al.

(10) Patent No.: US 8,065,929 B2
(45) Date of Patent: Nov. 29, 2011

(54) ENVIRONMENTAL MECHANICAL TEST APPARATUS

(75) Inventors: Todd Yakimoski, Beaumont (CA);
Bernadette Craster, Edmonton (CA);
Scott Jacobs, Issy les Moulineaux (FR);
Ahmed Hammami, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 387 days.

(21) Appl. No.: 12/435,531

(22) Filed: May 5, 2009

(65) Prior Publication Data

US 2009/0314107 A1    Dec. 24, 2009

(30) Foreign Application Priority Data

Jun. 23, 2008 (CA) .................................... 2635551

(51) Int. Cl.
*G01N 17/00* (2006.01)
(52) U.S. Cl. .................................................. 73/865.6
(58) Field of Classification Search ............ 73/865.6, 73/807, 818, 825, 37, 49.4; 374/51
See application file for complete search history.

(56) References Cited

U.S. PATENT DOCUMENTS 7,191,664 B2 * 3/2007 Thom et al. ................ 73/820
7,240,545 B1 * 7/2007 Jennings .................... 73/149

OTHER PUBLICATIONS

J.M. Hale and A.G. Gibson, An environmental chamber for tensile testing coupon specimens in the presence of aggressive media at elevated temperatures and pressures, Experimental Techniques, Sep./Oct. 1998, pp. 13-16.

Yusheng Yuan and Jim Goodson, HT/HP-Wet Thermomechanical Properties and HT/HP In-SITU Mechanical Test Method of High-Temperature Polymer Composites, Baker Oil Tools, Houston, Texas.

* cited by examiner

*Primary Examiner* — Jewel V Thompson
(74) *Attorney, Agent, or Firm* — Daren C. Davis; Wayne I. Kanak (57) ABSTRACT

An environmental mechanical test apparatus includes a pressure generation source and an isolation cylinder in fluid communication with the pressure generation source. The test apparatus further includes a pressure containment cell configured to receive a test specimen, an environmental chamber disposed about the pressure containment cell, and a load frame operably associated with the pressure containment cell. The pressure containment cell is in fluid communication with the pressure generation source and the isolation cylinder and includes a viewing window.

23 Claims, 5 Drawing Sheets

ENVIRONMENTAL MECHANICAL TEST APPARATUS

BACKGROUND OF THE INVENTION

1. Field of the Invention

The present invention relates to an apparatus for mechanically testing materials in environments of interest, such as harsh environments.

2. Description of Related Art

The development and qualification of materials for service in harsh environments requires testing the mechanical performance of such materials after, and/or during, sustained exposure to the harsh environment. Harsh environments include environments that exhibit extreme pressures and/or temperatures and/or wet environments that include corrosive fluids. Such harsh environments are often found in oilfield operations. Conventionally, materials that are being tested for service in harsh environments are often first subjected to a harsh environment then removed from the harsh environment for mechanical testing. Therefore, the true performance of the material of interest is not measured while the material is being subjected to the harsh environment. This is especially true for polymeric materials for which fluid ingress is usually reversible.

There are many designs of apparatuses for mechanically testing materials that are well known in the art; however, considerable shortcomings remain.

BRIEF SUMMARY OF THE INVENTION

In one aspect, the present invention provides an environmental mechanical test apparatus. The test apparatus includes a pressure generation source and an isolation cylinder in fluid communication with the pressure generation source. The test apparatus further includes a pressure containment cell configured to receive a test specimen. The pressure containment cell is in fluid communication with the pressure generation source and the isolation cylinder. The test apparatus may further include an environmental chamber disposed about the pressure containment cell and a load frame operably associated with the pressure containment cell. The pressure containment cell may also include a viewing window.

In another aspect of the present invention, a visual environmental mechanical test apparatus is provided. The test apparatus includes a load frame and a pressure containment cell defining a sealed cavity and comprising a first grip and a second grip for holding a specimen. The pressure containment cell is operably associated with the load frame to move the first grip with respect to the second grip to mechanically test the specimen. The test apparatus further includes a pressure generation source, an isolation cylinder in fluid communication with the pressure generation source and the pressure containment cell, and an environmental chamber disposed about the pressure containment cell. The test apparatus is configured to allow the specimen to be optically observed during testing.

In yet another aspect, the present invention provides a visual environmental mechanical test apparatus. The test apparatus includes a load frame comprising an actuator operably associated with a base, a pressure generation source, and an isolation cylinder defining a hydraulic fluid cavity in fluid communication with the pressure generation source and a testing fluid cavity, the hydraulic fluid cavity and the testing fluid cavity being separated by a piston. The test apparatus further includes a pressure containment cell, comprising a substantially transparent tube defining an interior space and a housing defining a bore in which the substantially transparent tube is disposed, the housing and the substantially transparent tube defining an annulus therebetween, the housing defining a viewing window and a fluid passageway extending to the annulus and in fluid communication with the pressure generation source. The pressure containment cell further includes an open end cap mechanically coupled with the housing and disposed at a first end of the bore of the housing, the open end cap defining a bore, a recess extending from the bore of the open end cap, and fluid passageway in fluid communication with the pressure generation source. The pressure containment cell further includes a sealing element disposed between the open end cap and the housing for inhibiting passage of fluid therebetween, a sealing element disposed between the open end cap and a first end of the substantially transparent tube for inhibiting passage of fluid therebetween, and a sealing element disposed in the recess of the open end cap. The pressure containment cell further includes an actuation rod extending through the bore of the open end cap, the actuation rod slidingly and sealingly engaged with the sealing element disposed in the recess of the end cap, the actuation rod mechanically coupled at a first end with the actuator of the load frame and terminating in a first grip disposed in the interior space defined by the substantially transparent tube. The pressure containment cell further includes a bellows attached to the open end cap and extending into the interior space defined by the substantially transparent tube, such that the bellows is disposed about the actuation rod and the fluid passageway defined by the open end cap is in fluid communication with an interior of the bellows. The pressure containment cell further includes a closed end cap mechanically coupled with the housing and the base of the load frame, the closed end cap disposed at a second end of the bore of the housing, defining a fluid passageway in fluid communication with the testing fluid cavity of the isolation cylinder, and terminating in a second grip disposed in the interior space defined by the substantially transparent tube. The pressure containment cell further includes a sealing element disposed between the closed end cap and the housing for inhibiting passage of fluid therebetween and a sealing element disposed between the closed end cap and a second end of the substantially transparent tube for inhibiting passage of fluid therebetween. The test apparatus further includes an environmental chamber disposed about the pressure containment cell, the environmental chamber comprising a viewing window generally aligned with the viewing window of the housing of the pressure containment cell.

The present invention provides significant advantages, including: (1) providing a means for testing the mechanical performance of a material after, and/or during, sustained exposure to environmental conditions of interest; (2) providing a means for testing the mechanical performance of a material while the material is exposed to a fluid of interest at a desired temperature and pressure; and (3) providing a means for visually observing an ongoing test of a material while the material is exposed to a fluid of interest at a desired temperature and pressure.

Additional objectives, features and advantages will be apparent in the written description which follows.

BRIEF DESCRIPTION OF THE DRAWINGS

The novel features characteristic of the invention are set forth in the appended claims. However, the invention itself, as well as a preferred mode of use and further objectives and advantages thereof, will best be understood by reference to the following detailed description when read in conjunction with the accompanying drawings, in which the leftmost significant digit in the reference numerals denotes the first figure in which the respective reference numeral appears, wherein:

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention represents a visual environmental mechanical test apparatus for testing one or more mechanical properties of a material while the material is submerged in a fluid at a desired temperature and pressure. While the invention is not so limited, the test apparatus is used in certain embodiments to determine the tension, compression, shear, and/or fatigue properties of a material. The test apparatus allows a specimen of the material being tested to be visually inspected as the test is being conducted. The visual environmental mechanical test apparatus is particularly useful for testing materials in an environment that simulates the environment found in downhole oilfield operations.

Figure 1:
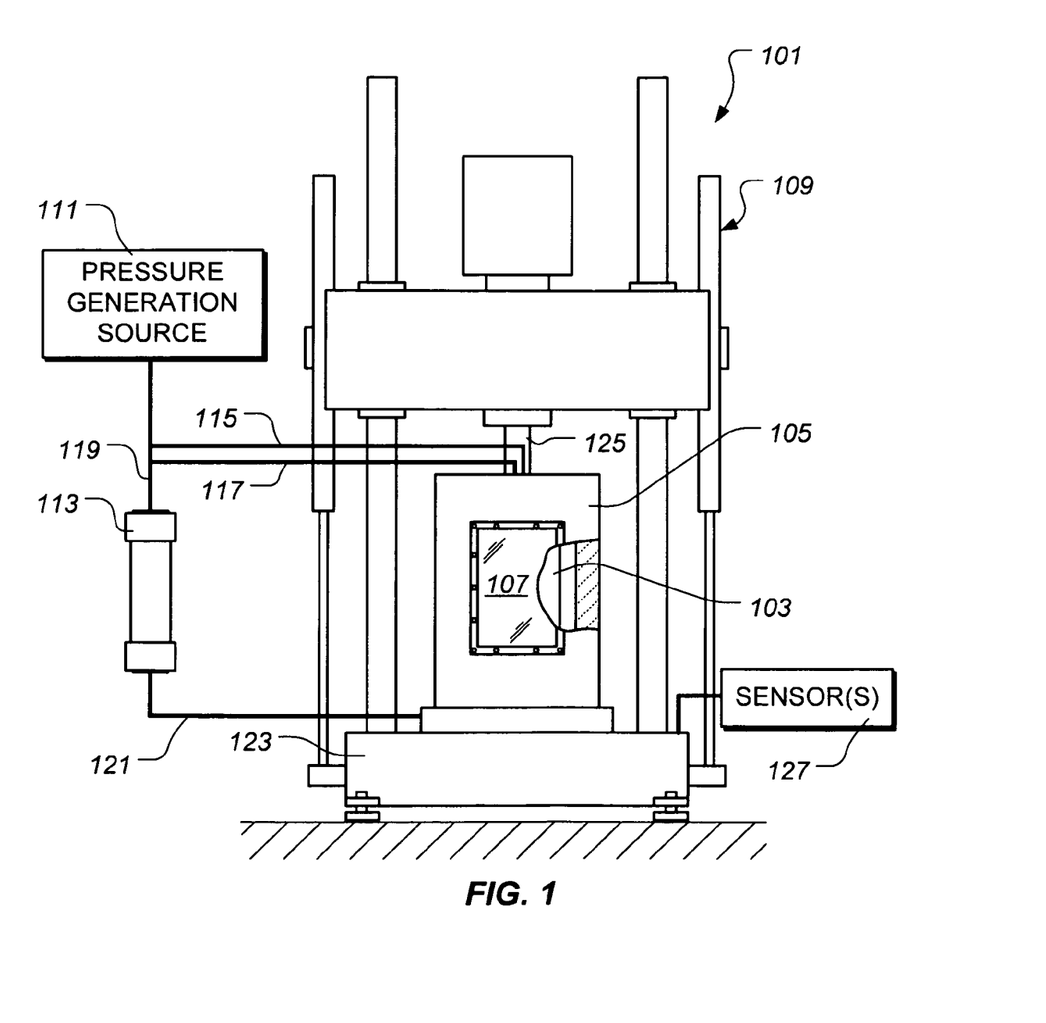
FIG. 1 is a stylized, front, elevational view of an illustrative embodiment of a visual mechanical test apparatus of the present invention.

FIG. 1 is a stylized, front, elevational view of a visual environmental mechanical test apparatus 101. In the illustrated embodiment, test apparatus 101 comprises a pressure containment cell 103 disposed in an environmental chamber 105. It should be noted that, in FIG. 1, a portion of environmental chamber 105 is removed to reveal pressure containment cell 103. Environmental chamber 105 thermally insulates pressure containment cell 103 and, in one embodiment, includes a viewing window 107 that allows pressure containment cell 103 to be viewed during operation. In other embodiments, however, environmental chamber 105 omits viewing window 107. In one embodiment, environmental chamber 105 includes means for heating pressure containment cell 103 and a test specimen (not shown in FIG. 1) disposed therein. In other embodiments, pressure containment cell 103 includes a means for heating the test specimen disposed in pressure containment cell 103.

Still referring to FIG. 1, pressure containment cell 103 is held in a load frame 109, which operates on the test specimen (not shown in FIG. 1) disposed in pressure containment cell 103 during mechanical testing operations. Depending upon the implementation, load frame 109 may be configured to provide force and displacement measurement. Alternatively, non-contact extensometer technology may be employed via viewing window 107 of environmental chamber 105 and a viewing window 323 (shown in FIGS. 3 and 4) of pressure containment cell 103. As is discussed in greater detail herein, pressure containment cell 103 is in fluid communication with a pressure generation source 111 via fluid transmission lines 115 and 117 and is in fluid communication with an isolation cylinder 113 via a fluid transmission line 121. Isolation cylinder 113 is in fluid communication with pressure generation source 111 via a fluid transmission line 119.

Figure 2:
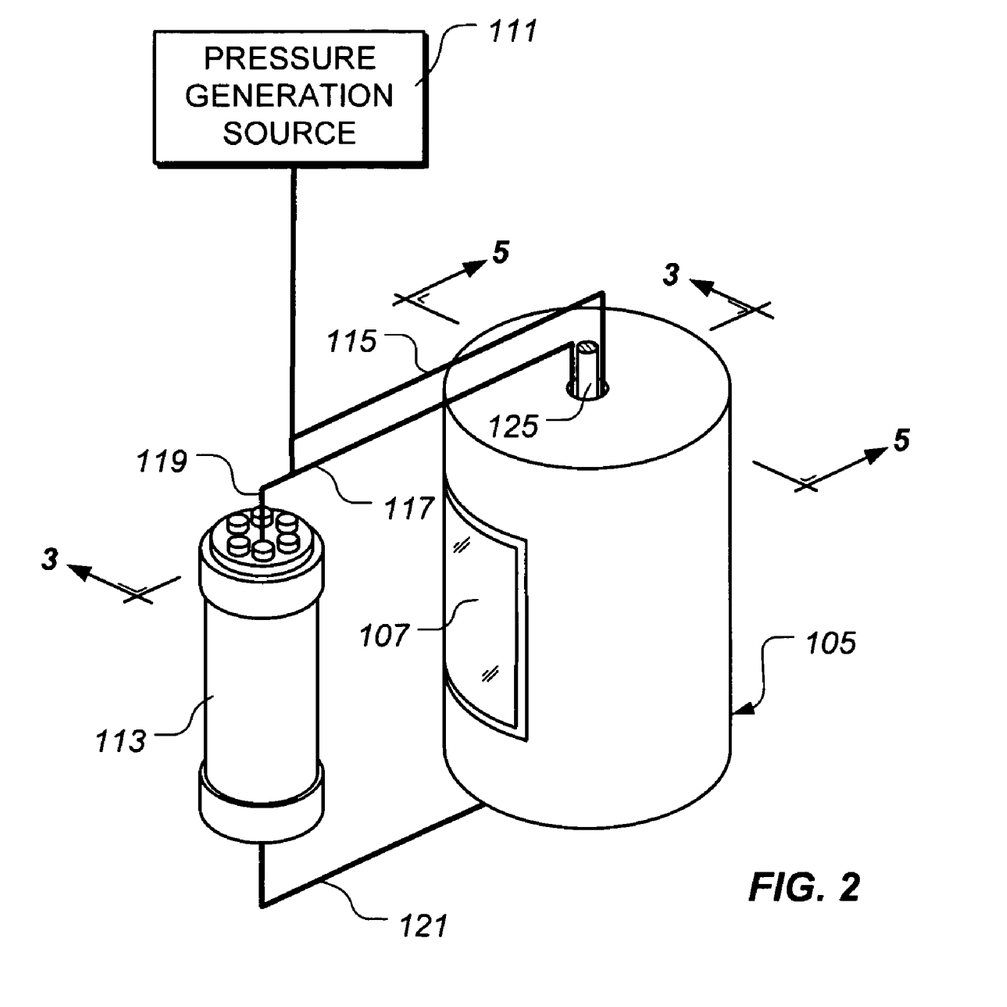
FIG. 2 is a stylized, perspective view of illustrative embodiments of an isolation cylinder and an environmental chamber housing a pressure containment cell, both of the test apparatus of FIG. 1.
Figure 3:
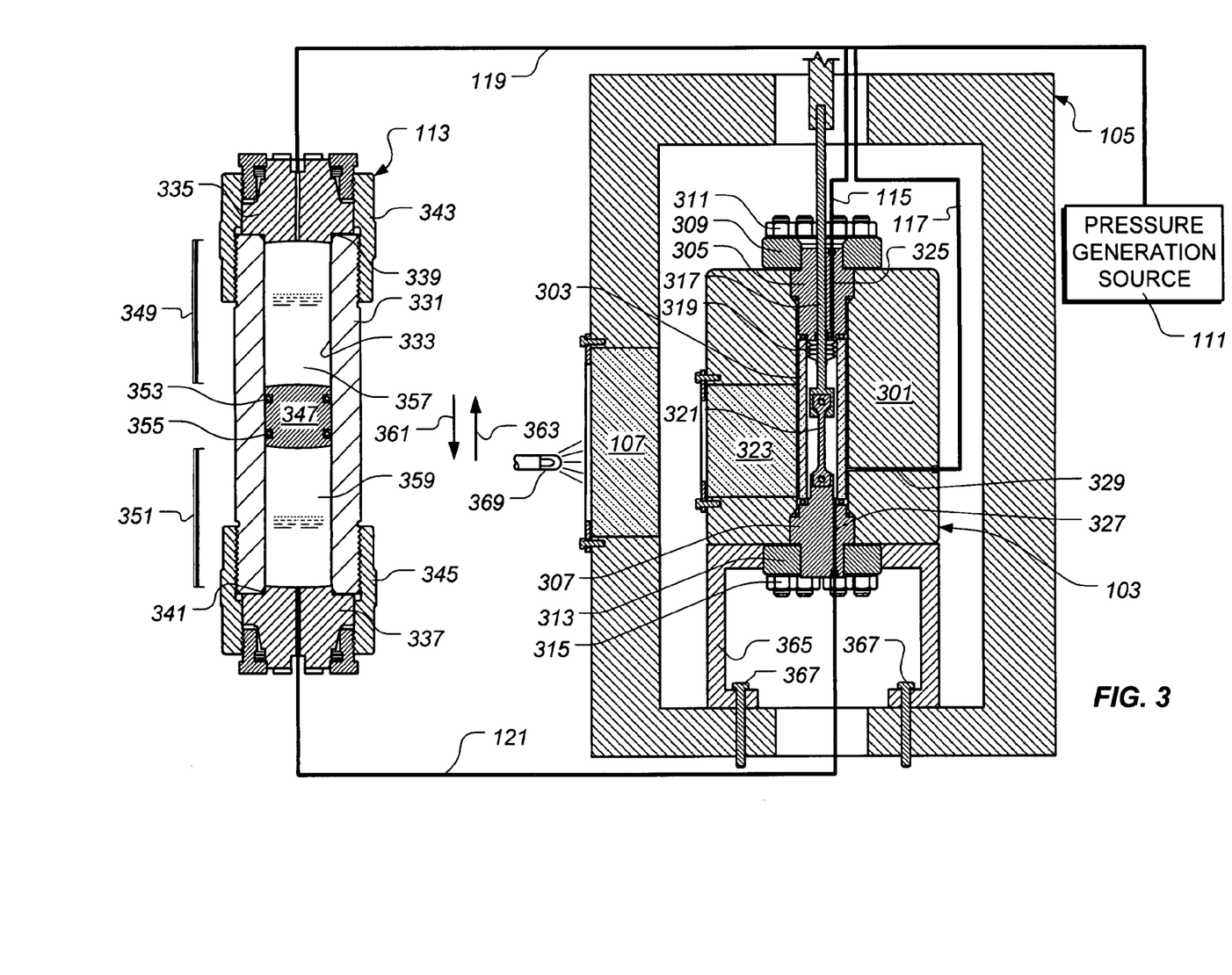
FIG. 3 is a cross-sectional view of the isolation cylinder, environmental chamber, and pressure containment cell of FIG. 2, taken along section line 3-3 in FIG. 2.
Figure 4:
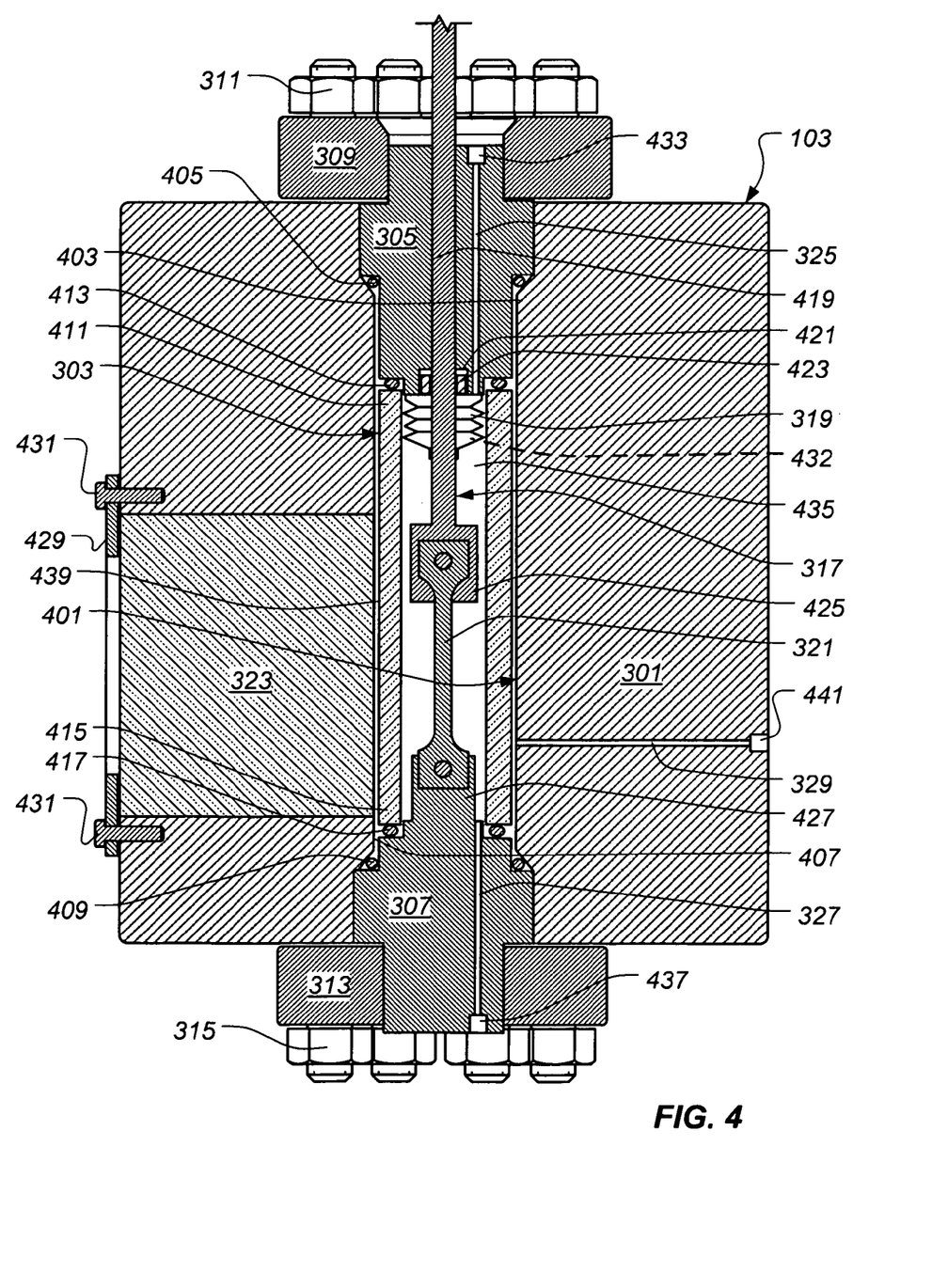
FIG. 4 is an enlarged cross-sectional view of the pressure containment cell of FIG. 3.

FIG. 2 depicts a stylized, perspective view of isolation cylinder 113 and environmental chamber 105 with pressure containment cell 103 disposed therein. FIG. 3 depicts a cross-sectional view, taken along section line 3-3 in FIG. 2, of isolation cylinder 113, environmental chamber 105, and pressure containment cell 103. FIG. 4 is an enlarged, cross-sectional view of pressure containment cell 103, corresponding to the view of FIG. 3. Referring to FIG. 4, pressure containment cell 103 comprises a housing 301 defining a bore 401 therethrough. A substantially transparent tube 303 is disposed in bore 401. Bore 401 is fluidly sealed at a first end 403 by an open end cap 305 in conjunction with a sealing element 405. Bore 401 is fluidly sealed at a second end 407 by a closed end cap 307 in conjunction with a sealing element 409. Tube 303 is sealed to open end cap 305 at a first end 411 of tube 303 by a sealing element 413. Tube 303 is sealed to closed end cap 307 at a second end 415 of tube 303 by a sealing element 417. In the embodiment depicted in FIGS. 3 and 4, sealing elements 405, 409, 413, and 417 are O-rings. However, other sealing element configurations are contemplated by the present invention. Open end cap 305 is held in sealing relationships with housing 301 and tube 303 by a first clamp ring 309, which is attached to housing 301 by a first set of clamp ring studs and nuts 311. Closed end cap 307 is held in sealing relationships with housing 301 and tube 303 by a second clamp ring 313, which is attached to housing 301 by a second set of clamp ring studs and nuts 315. Other means of retaining end caps 305 and 307, such as threaded retainers, are contemplated by the present invention.

Open end cap 305 defines a bore 419 and a recess 421 extending from bore 419. A sealing element 423 is disposed in recess 421. An actuation rod 317 extends through bore 419 of open end cap 305 and sealing element 423, terminating in a grip 425. Sealing element 423 is slidingly but sealingly engaged with actuation rod 317 to provide a fluid seal between actuation rod 317 and open end cap 305. A bellows 319 is attached to open end cap 305 and attached, by, for example, welding or friction, to actuation rod 317 to aid in isolating sealing element 423 from fluid introduced into tube 303, as discussed in greater detail herein. Closed end cap 307 terminates in a grip 427. Grips 425 and 427 are configured to hold a specimen 321 for testing. In the embodiment shown in FIGS. 3 and 4, specimen 321 is a tensile specimen and grips 425 and 427 are configured to hold a tensile specimen. The scope of the present invention, however, is not so limited. The particular configurations of grips 425 and 427 are implementation specific, as test apparatus 101 (shown in FIG. 1) can be used to test a variety of mechanical properties of a specimen, not just the tensile properties of specimen 321. For example, grips 425 and 427 may be configured to hold a compression specimen, a shear specimen, or the like. Actuation rod 317 is mechanically coupled with a movable actuator 125 of load frame 109 (shown in FIG. 1). Actuator 125 imparts mechanical forces on specimen 321 during mechanical testing of specimen 321 or the like. Housing 301 includes substantially transparent viewing window 323 for visually inspecting specimen 321, or another specimen, held by grips 425 and 427 during testing operations. In the illustrated embodiment, viewing window 323 is held in place by a cover plate 429 and studs 431, although other ways of retaining window 323 are contemplated by the present invention.

Still referring to FIG. 4, open end cap 305 further defines a fluid passageway 325 through which fluid is transmitted from pressure generation source 111 (shown in FIGS. 1-3) to an interior space 432 defined by bellows 319 and open end cap 305. Open end cap 305 further defines a fitting 433 that fluidly couples fluid transmission line 115 to fluid passageway 325 of open end cap 305. Closed end cap 307 defines a fluid passageway 327 through which fluid is transmitted from isolation cylinder 113 (shown in FIGS. 1-3) to an interior space 435 of tube 303. Closed end cap 307 further defines a fitting 437 that fluidly couples fluid transmission line 121 (shown in FIGS. 1-3) to fluid passageway 327 of closed end cap 307. Housing 301 defines a fluid passageway 329 through which fluid is transmitted from pressure generation source 111 (shown in FIGS. 1-3) to an annulus 439 between tube 303 and housing 301. Housing 301 further defines a fitting 441 that fluidly couples fluid transmission line 117 (shown in FIGS. 1-3) to fluid passageway 329 of housing 301.

Turning now to the embodiment of FIG. 3, isolation cylinder 113 comprises a barrel 331 defining a bore 333 therethrough. End caps 335 and 337 seal ends of bore 333 via sealing elements 339 and 341. End caps 335 and 337 are retained on barrel 331 by retainers 343 and 345, respectively, which are threadedly engaged with barrel 331. A piston 347 is slidingly disposed in bore 333 of barrel 331. Barrel 331, end cap 335, and piston 347 define a hydraulic fluid cavity 349. Barrel 331, end cap 337, and piston 347 define a testing fluid cavity 351. Sealing elements 353 and 355 inhibit fluid from traveling between hydraulic fluid cavity 349 and testing fluid cavity 351. Hydraulic fluid cavity 349 contains substantially transparent hydraulic fluid 357. Testing fluid cavity 351 contains testing fluid 359 in which specimen 321 is being tested. Testing fluid 359 can comprise any fluid suitable for use in test apparatus 101 that is desirable for testing specimen 321, such as harsh fluids found in downhole oilfield environments.

Still referring to FIG. 3, testing fluid cavity 351 of isolation cylinder 113 is in fluid communication with interior space 435 (shown in FIG. 4) of tube 303 via fluid transmission line 121 and fluid passageway 327 of closed end cap 307. Hydraulic fluid 357 in hydraulic fluid cavity 349 of isolation cylinder 113 is maintained at a desired pressure by pressure generation source 111. Pressure generation source 111 is in fluid communication with interior space 432 (shown in FIG. 4) defined by bellows 319 and open end cap 305 via fluid transmission line 115 and fluid passageway 325 of open end cap 305. Pressure generation source 111 is in fluid communication with annulus 439 (shown in FIG. 4) between housing 301 and tube 303.

In operation, pressure generation source 111 provides substantially transparent, hydraulic fluid 357 at a common pressure to hydraulic fluid cavity 349 of isolation cylinder 113, to interior space 432 (shown in FIG. 4) defined by bellows 319 and open end cap 305, and to annulus 439 (shown in FIG. 4) between housing 301 and tube 303. Pressurized hydraulic fluid 357 acts upon piston 347 of isolation cylinder 113 to regulate the pressure of testing fluid 359 provided to interior space 435 (shown in FIG. 4) of tube 303. Thus, as the pressure of hydraulic fluid 357 is increased by pressure generation source 111, piston 347 of isolation cylinder 113 moves in a direction generally corresponding to arrow 361 to decrease the volume of testing fluid cavity 351 of isolation cylinder 113 and increase the pressure of testing fluid 359. Correspondingly, as the pressure of hydraulic fluid 357 is decreased by pressure generation source 111, piston 347 of isolation cylinder 113 moves in a direction generally corresponding to arrow 363 to increase the volume of testing fluid cavity 351 of isolation cylinder 113 and reduce the pressure of testing fluid 359. During operation, hydraulic fluid 357 disposed in interior space 432 (shown in FIG. 4), defined by bellows 319 and open end cap 305, and hydraulic fluid 357 disposed in annulus 439 (shown in FIG. 4) between housing 301 and tube 303 is maintained at substantially the same pressure as the pressure of testing fluid 359 disposed in interior space 435 of tube 303. Moreover, the relative volumes of hydraulic fluid 357 and testing fluid 359 disposed in pressure containment cell 103 can vary without changing the overall system pressure, such as when the shape of bellows 319 changes during testing.

Referring to FIGS. 1 and 3, in one embodiment, pressure containment cell 103 is attached to a fixed base 123 of load frame 109 via a bracket 365 and fasteners 367. The present invention, however, contemplates other means for attaching pressure containment cell 103 to base 123 of load frame 109. As shown in FIG. 3, viewing window 107 of environmental chamber 105 and viewing window 323 of housing 301 are generally aligned during operation of test apparatus 101 to allow visual inspection of specimen 321.

Figure 5:
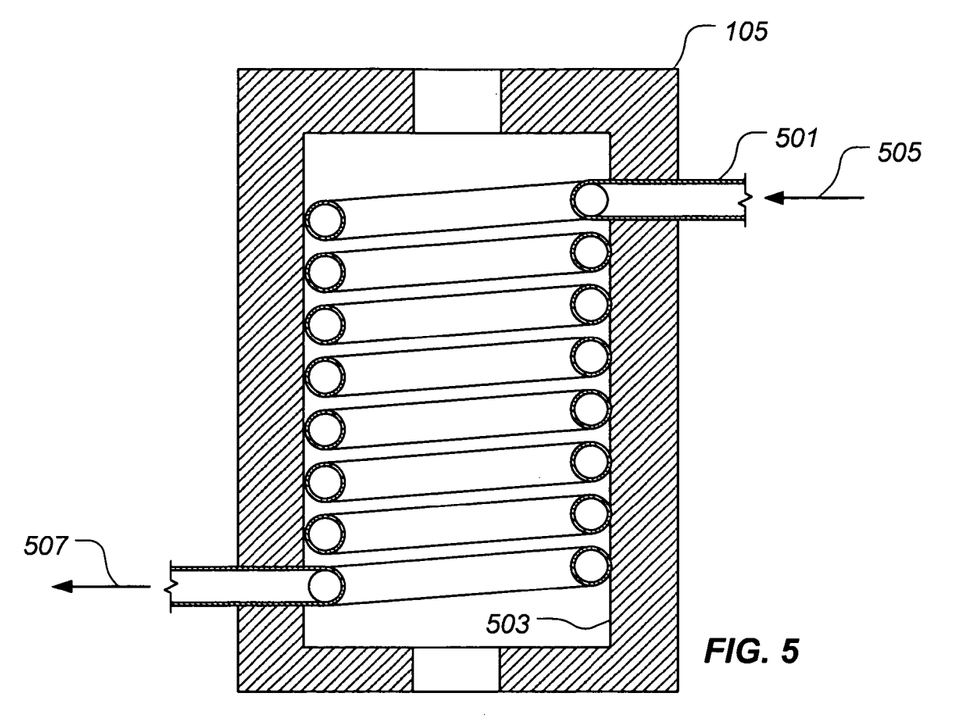
FIG. 5 is a cross-sectional view of one particular embodiment of the environmental chamber of FIG. 2, taken along section line 5-5 in FIG. 2.
Figure 6:
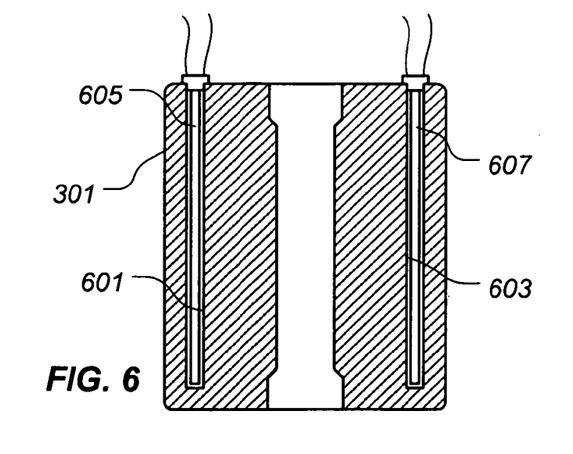
FIG. 6 is a cross-sectional view of one particular embodiment of a housing of the pressure containment cell of FIG. 3, corresponding to the view of FIG. 5.

As noted herein, test apparatus 101 (shown in FIG. 1) includes a means for heating specimen 321 (shown in FIGS. 3 and 4). FIGS. 5 and 6 depict exemplary embodiments of such a means for heating specimen 321. It should be noted that FIGS. 5 and 6 are stylized, cross-sectional views taken along section line 5-5 in FIG. 2 and depict only environmental chamber 105 and housing 301 of pressure containment cell 103, respectively. In the embodiment of FIG. 5, environmental chamber 105 includes a heating fluid conduit 501, which, in the illustrated embodiment, is disposed on an inner surface 503 of environmental chamber 105 so as not to obscure viewing window 107. Heated fluid is circulated, as indicated by arrows 505 and 507, through heating fluid conduit 501, which heats pressure containment cell 103 and specimen 321. In the embodiment of FIG. 6, housing 301 of pressure containment cell 103 defines cavities 601 and 603 in which electrically-powered heating elements 605 and 607, respectively, are disposed. Note that electrically-powered heating elements 605 and 607 are not shown in cross-section in FIG. 6. Electrical current is applied to each of heating elements 605 and 607 to heat housing 301 and, thus, specimen 321. It should be noted that the embodiments shown in FIGS. 5 and 6 are merely exemplary of the many different configurations of heating fluid conduits and electrically-powered heating elements, such as heating blankets, contemplated by the present invention. The embodiments of FIGS. 5 and 6 are also only exemplary of the various means for heating specimen 321 contemplated by the present invention.

It should be noted that the present invention contemplates additional features of test apparatus 101. For example, closed end cap 307, shown in FIGS. 3 and 4, may include a mixer, such as a magnetic mixer, for mixing testing fluid 359, shown in FIG. 3. Test apparatus 101 may also include one or more sensors, such as sensors 127 of FIG. 1, to measure characteristics or parameters of interest during testing, such as specimen strain, fluid pressure, specimen temperature, and the like. Such sensors may be "hard-wired" types or wireless varieties.

Specimen 321, or any other such specimen, may be subjected to various temperatures, pressures, and testing fluid types over any desired period of time without removing specimen 321 from test apparatus 101. For example, specimen 321 or the like may be subjected to a particular type of harsh fluid found in downhole oilfield operations at pressures of up to about 103 megapascals (15,000 pounds/square inch) and at temperatures up to about 232 degrees Celsius (450 degrees Fahrenheit) for any desired period of time. The visual observation of specimen 321 or the like may be enhanced through the use of a lamp, such as a lamp 369, as shown in FIG. 3.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present invention is shown in a limited number of forms, it is not limited to just these forms, but is amenable to various changes and modifications.

What is claimed is:

1. An environmental mechanical test apparatus, comprising:
    a pressure generation source;
    an isolation cylinder in fluid communication with the pressure generation source; and
    a pressure containment cell configured to receive a test specimen, the pressure containment cell in fluid communication with the pressure generation source and the isolation cylinder.

2. The environmental mechanical test apparatus of claim 1, further comprising an environmental chamber disposed about the pressure containment cell.

3. The environmental mechanical test apparatus of claim 1, further comprising a load frame operably associated with the pressure containment cell.

4. The environmental mechanical test apparatus of claim 1, wherein the pressure containment cell includes a viewing window.

5. The environmental mechanical test apparatus of claim 1, wherein the isolation cylinder defines a hydraulic fluid cavity and a testing fluid cavity separated by a piston.

6. The environmental mechanical test apparatus of claim 3, wherein:
    the load frame comprises an actuator operably associated with a base; and
    the pressure containment cell comprises:
        a substantially transparent tube defining an interior space;
        a housing defining a housing bore therethrough in which the tube is disposed, and a fluid passageway in fluid communication with the pressure generation source extending to an annulus defined by the housing and the tube;
        an open end cap sealingly disposed at a first end of the housing bore and defining an end cap bore therethrough;
        a closed end cap sealingly disposed at a second end of the housing bore, terminating in a grip disposed in the interior space of the tube, and mechanically coupled with the base of the load frame, the closed end cap defining a fluid passageway in fluid communication with a testing fluid cavity in the isolation cylinder and extending to the interior space of the tube; and
        an actuation rod slidingly and sealingly extending through the end cap bore, terminating at a first end in a grip disposed in the interior space of the tube and mechanically coupled at a second end with the actuator of the load frame.

7. The environmental mechanical test apparatus of claim 6, further comprising:
    a bellows mechanically coupled with the open end cap and disposed about the actuation rod, such that the bellows and the open end cap define an interior space;
    wherein the open end cap defines a fluid passageway, in fluid communication with the pressure generation source, extending to the interior space defined by the bellows and the open end cap.

8. The environmental mechanical test apparatus of claim 5, wherein the isolation cylinder comprises:
    a barrel;
    a first end cap sealingly disposed at a first end of the barrel; and
    a second end cap sealingly disposed at a second end of the barrel;
    wherein the piston is disposed in the barrel, such that the piston, the first end cap, and the barrel define the hydraulic fluid cavity, and the piston, the second end cap, and the barrel define the testing fluid cavity;
    wherein the first end cap defines a passageway in fluid communication with the pressure generation source extending to the hydraulic fluid cavity; and
    wherein the second end cap defines a passageway in fluid communication with the pressure containment cell extending to the testing fluid cavity.

9. The environmental mechanical test apparatus of claim 5, wherein substantially transparent hydraulic fluid is supplied by the pressure generation source and is disposed in the hydraulic fluid cavity of the isolation cylinder.

10. The environmental mechanical test apparatus of claim 5, wherein a downhole oilfield fluid is disposed in the testing fluid cavity and is fluidly communicated under pressure to the pressure containment cell.

11. The environmental mechanical test apparatus of claim 1, wherein the pressure containment cell comprises means for heating the test specimen.

12. The environmental mechanical test apparatus of claim 11, wherein the means for heating the test specimen comprises one of a heating fluid conduit and an electrically-powered heating element.

13. The environmental mechanical test apparatus of claim 2, wherein the environmental chamber comprises means for heating the test specimen.

14. The environmental mechanical test apparatus of claim 13, wherein the means for heating the test specimen comprises one of a heating fluid conduit and an electrically-powered heating element.

15. The environmental mechanical test apparatus of claim 4, wherein the environmental chamber includes a viewing window generally aligned with the viewing window of the pressure containment cell.

16. A visual environmental mechanical test apparatus, comprising:
- a load frame;
- a pressure containment cell defining a sealed cavity and comprising a first grip and a second grip for holding a specimen, the pressure containment cell being operably associated with the load frame to move the first grip with respect to the second grip to mechanically test the specimen;
- a pressure generation source;
- an isolation cylinder in fluid communication with the pressure generation source and the pressure containment cell; and
- an environmental chamber disposed about the pressure containment cell;
- wherein the test apparatus is configured to allow the specimen to be optically observed during testing.

17. The visual environmental mechanical test apparatus of claim 16, wherein the load frame comprises an actuator operably associated with a base and the pressure containment cell comprises an actuation rod slidingly and sealingly extending into the sealed cavity of the pressure containment cell, the actuation rod being mechanically coupled with the actuator of the load frame and terminating in the first grip.

18. The visual environmental mechanical test apparatus of claim 16, wherein the isolation cylinder defines a hydraulic fluid cavity and a testing fluid cavity separated by a piston, such that the hydraulic fluid cavity is in fluid communication with the pressure generation source and the testing fluid cavity is in fluid communication with the sealed cavity of the pressure containment cell.

19. The visual environmental mechanical test apparatus of claim 16, wherein the pressure containment cell comprises a housing and a substantially transparent tube disposed in the housing, the substantially transparent tube defining the sealed cavity; and
- wherein the environmental chamber and the housing of the pressure containment cell each comprise a viewing window.

20. The visual environmental mechanical test apparatus of claim 19, wherein:
- the pressure generation source provides substantially transparent hydraulic fluid to an annulus between the housing and the substantially transparent tube; and
- the isolation cylinder provides testing fluid to the sealed cavity of the pressure containment cell.

21. The visual environmental mechanical test apparatus of claim 16, wherein the test apparatus is configured to test at least one of tensile, compression, shear, and fatigue properties of the specimen.

22. A visual environmental mechanical test apparatus, comprising:
- a load frame comprising an actuator operably associated with a base;
- a pressure generation source;
- an isolation cylinder defining a hydraulic fluid cavity in fluid communication with the pressure generation source and a testing fluid cavity, the hydraulic fluid cavity and the testing fluid cavity being separated by a piston;
- a pressure containment cell, comprising:
  - a substantially transparent tube defining an interior space;
  - a housing defining a housing bore in which the substantially transparent tube is disposed, the housing and the substantially transparent tube defining an annulus therebetween, the housing defining a viewing window and a fluid passageway extending to the annulus and in fluid communication with the pressure generation source;
  - an open end cap mechanically coupled with the housing and disposed at a first end of the housing bore, the open end cap defining an end cap bore, a recess extending from the end cap bore, and a fluid passageway in fluid communication with the pressure generation source;
  - a sealing element disposed between the open end cap and the housing for inhibiting passage of fluid therebetween;
  - a sealing element disposed between the open end cap and a first end of the substantially transparent tube for inhibiting passage of fluid therebetween;
  - a sealing element disposed in the recess of the open end cap;
  - an actuation rod extending through the end cap bore, the actuation rod slidingly and sealingly engaged with the sealing element disposed in the recess of the open end cap, the actuation rod mechanically coupled at a first end with the actuator of the load frame and terminating in a first grip disposed in the interior space defined by the substantially transparent tube;
  - a bellows attached to the open end cap and extending into the interior space defined by the substantially transparent tube, such that the bellows is disposed about the actuation rod and the fluid passageway defined by the open end cap is in fluid communication with an interior of the bellows;
  - a closed end cap mechanically coupled with the housing and the base of the load frame, the closed end cap disposed at a second end of the housing bore, defining a fluid passageway in fluid communication with the testing fluid cavity of the isolation cylinder, and terminating in a second grip disposed in the interior space defined by the substantially transparent tube;
  - a sealing element disposed between the closed end cap and the housing for inhibiting passage of fluid therebetween; and
  - a sealing element disposed between the closed end cap and a second end of the substantially transparent tube for inhibiting passage of fluid therebetween; and
  - an environmental chamber disposed about the pressure containment cell, the environmental chamber comprising a viewing window generally aligned with the viewing window of the housing of the pressure containment cell.

23. The visual environmental mechanical test apparatus of claim 22, wherein the isolation cylinder comprises:
- a barrel;
- a first end cap attached to a first end of the barrel;
- a sealing element disposed between the first end cap and the barrel for inhibiting passage of fluid therebetween;
- a second end cap attached to a second end of the barrel;

a sealing element disposed between the second end cap and the barrel for inhibiting passage of fluid therebetween; and at least one sealing element operably associated with the piston for inhibiting passage of fluid between the hydraulic fluid cavity and the testing fluid cavity;

wherein the piston is disposed in the barrel, such that the piston, the first end cap, and the barrel define the hydraulic fluid cavity and the piston, the second end cap, and the barrel define the testing fluid cavity;

wherein the first end cap defines a passageway in fluid communication with the pressure generation source extending to the hydraulic fluid cavity; and wherein the second end cap defines a passageway in fluid communication with the pressure containment cell extending to the testing fluid cavity.

* * * * *